United States Patent
Chen et al.

(10) Patent No.: US 11,169,136 B2
(45) Date of Patent: Nov. 9, 2021

(54) METHOD FOR MEASURING CORROSION-EXPANSION FORCE DURING CRACKING OF CONCRETE DUE TO CORROSION AND EXPANSION OF REINFORCING STEEL

(71) Applicant: QINGDAO UNIVERSITY OF TECHNOLOGY, Shandong (CN)

(72) Inventors: Fanxiu Chen, Qingdao (CN); Bin Zhang, Qingdao (CN); Pengfei Guo, Qingdao (CN); Zuquan Jin, Qingdao (CN)

(73) Assignee: QINGDAO UNIVERSITY OF TECHNOLOGY, Qingdao (CN)

( * ) Notice: Subject to any disclaimer, the term of this patent is extended or adjusted under 35 U.S.C. 154(b) by 0 days.

(21) Appl. No.: 17/049,194

(22) PCT Filed: Nov. 25, 2019

(86) PCT No.: PCT/CN2019/120501
§ 371 (c)(1),
(2) Date: Oct. 20, 2020

(87) PCT Pub. No.: WO2020/177402
PCT Pub. Date: Sep. 10, 2020

(65) Prior Publication Data
US 2021/0199637 A1    Jul. 1, 2021

(30) Foreign Application Priority Data

Mar. 4, 2019  (CN) .......................... 201910159067.2

(51) Int. Cl.
*G01B 11/16*     (2006.01)
*G01N 33/38*     (2006.01)
(Continued)

(52) U.S. Cl.
CPC .......... *G01N 33/383* (2013.01); *G01L 5/1627* (2020.01); *G01N 17/00* (2013.01);
(Continued)

(58) Field of Classification Search
CPC .... G01N 33/383; G01N 17/00; G01L 5/1627; G06T 7/001; G06T 2207/30132; H04N 5/247; H04N 5/2256
See application file for complete search history.

(56) References Cited

U.S. PATENT DOCUMENTS

2018/0283847 A1*  10/2018  Hatahori ............... G01M 7/025

FOREIGN PATENT DOCUMENTS

| GN | 104330023 A | 2/2015 |
| GN | 106770360 A | 5/2017 |

(Continued)

OTHER PUBLICATIONS

Feb. 25, 2020 Written Opinion of the International Searching Authority issued in International Patent Application No. PCT/CN2019/120501.
(Continued)

*Primary Examiner* — Patrick E Demosky
(74) *Attorney, Agent, or Firm* — Oliff PLC (57) ABSTRACT

A method for measuring corrosion-expansion force during cracking of concrete due to corrosion and expansion of reinforcing steel; wherein, deformation on a surface of reinforced concrete is photographed based on a digital image correlation (DIC) method, a full-field displacement and a full-field strain on a surface of the concrete are analyzed and calculated, a relationship between corrosion-expansion force and the strain on the surface of the concrete is found through an established theoretical model, and corrosion-expansion force of reinforcing steel and a change rule of the corrosion-expansion force are calculated. Therefore, the
(Continued)

method is simple and includes with safe and reliable operations, scientific principles, and low costs, so that a change in corrosion-expansion force during corrosion and expansion of reinforced concrete can be monitored in real time.

3 Claims, 3 Drawing Sheets

(51) Int. Cl.
  *G01L 5/1627* (2020.01)
  *G01N 17/00* (2006.01)
  *G06T 7/00* (2017.01)
  *H04N 5/225* (2006.01)
  *H04N 5/247* (2006.01)
(52) U.S. Cl.
  CPC ........... *G06T 7/001* (2013.01); *H04N 5/2256* (2013.01); *H04N 5/247* (2013.01); *G06T 2207/30132* (2013.01)

(56) References Cited

FOREIGN PATENT DOCUMENTS

| | | |
|---|---|---|
| GN | 108332891 A | 7/2018 |
| GN | 108489413 A | 9/2018 |
| GN | 109669028 A | 4/2019 |
| JP | 2008-268123 A | 11/2008 |

OTHER PUBLICATIONS

Gao et al.; "Measurement of displacement and strain fields of fatigue crack tip under resonant loading based on DIC method;" Ordnance Material Science and Engineering; 2016; pp. 16-22; vol. 29, No. 1.

Feb. 25, 2020 Search Report issued in International Patent Application No. PCT/CN2019/120501.

\* cited by examiner

METHOD FOR MEASURING CORROSION-EXPANSION FORCE DURING CRACKING OF CONCRETE DUE TO CORROSION AND EXPANSION OF REINFORCING STEEL

BACKGROUND

Technical Field

The present invention belongs to the technical field of concrete corrosion, and relates to a method for measuring corrosion-expansion force during corrosion of reinforcing steel in concrete through non-destructive monitoring, and in particular, to a method for measuring corrosion-expansion force during cracking of concrete due to corrosion and expansion of reinforcing steel. Therefore, a digital image correlation (DIC) method is used to monitor information such as a displacement and a strain of a surface of reinforced concrete in real time, and corrosion-expansion force of reinforcing steel in concrete is derived through an established theoretical model, to analyze a change rule of the corrosion-expansion force of the reinforcing steel during corrosion.

Related Art

In the early 19th century, reinforced concrete materials brought a revolution in the construction field, and more and more buildings were built with the reinforced concrete materials. Reinforcing steel has good tensile properties, and concrete has good tensile strength and plasticity. In addition, the two have excellent adhesion, so that the concrete can be combined with the reinforcing steel. The reinforced concrete materials fully utilize the advantages of the concrete and the reinforcing steel and make up for each other's deficiencies. The reinforcing steel embedded in the concrete can increase tensile strength and bending strength of the concrete, and the concrete provides an alkaline environment for the reinforcing steel to prevent corrosion of the reinforcing steel. A concrete protective layer can also function well in heat insulation, to effectively prevent the reinforcing steel from deteriorating due to heat. These characteristics make the reinforced concrete materials become the most common building materials in industry and civil use. The alkaline environment formed by concrete hydrates and a passivation film on a surface of the reinforcing steel can protect the reinforcing steel from corrosion. Therefore, it is generally believed that the reinforced concrete structure will not rust due to natural causes, and the concrete protective layer will not crack. However, with an increase in application scenarios of the reinforced concrete materials, the reinforced concrete structure serving in humid environments such as a coastal port is corroded by chloride salts to cause the alkaline environment of the concrete to fail and the passivation film of the reinforcing steel to rupture, resulting in the corrosion of the reinforcing steel. Eventually, corrosion products of the reinforcing steel cause cracking of the concrete protective layer. Therefore, in recent years, the corrosion of the reinforcing steel has been widely concerned and valued by many scholars, and has become a hot topic of concern for researchers at home and abroad.

At present, for the research on corrosion-expansion force of the reinforcing steel, there are three main ways to obtain the corrosion-expansion force of the reinforcing steel: 1. The corrosion-expansion force is obtained through internal data of the reinforced concrete structure such as thickness of the corrosion products of the reinforcing steel and a carbonization depth of the concrete. 2. An instrument is embedded in a test piece to obtain a current of the reinforcing steel or a strain to calculate the corrosion-expansion force. 3. Instantaneous corrosion-expansion force of cracking is obtained by establishing a model. However, these existing methods cannot monitor a change in the corrosion-expansion force in real time, and are more difficult to implement and costly. Therefore, it is urgent to design a simple and low-cost method measuring corrosion-expansion force during cracking of concrete due to corrosion and expansion of reinforcing steel. Non-contact non-destructive monitoring of a DIC method can effectively make up for the shortcomings of the existing method and monitor a change process in real time, making it possible to non-destructively monitor the corrosion-expansion force during the cracking of the concrete.

SUMMARY

The present invention provides a simple and easy-to-operate method for measuring corrosion-expansion force of reinforced concrete during corrosion and expansion, to overcome the shortcomings of the prior art. In the method, deformation on a surface of reinforced concrete is photographed based on a DIC method, a full-field displacement and a full-field strain on a surface of the concrete are analyzed and calculated, a relationship between corrosion-expansion force and the strain on the surface of the concrete is found through an established theoretical model, and corrosion-expansion force of reinforcing steel and a change rule of the corrosion-expansion force are calculated.

In order to achieve the above object, specific steps of measuring corrosion-expansion force of reinforced concrete during corrosion and expansion in the present invention are:

(1) first fixing reinforcing steel in the middle of a 100 mm×100 mm×300 mm mold, using stainless reinforcing steel as an electrode for electrical acceleration, and then pouring mixed concrete, so that after a cross section of the reinforcing steel is flush with a surface of the concrete, the reinforcing steel and the concrete are placed on a vibration table and vibrated for 5 minutes, and are demoulded after 24 hours and placed in a steam curing room for curing for two months to obtain a concrete test block; and pasting strain gauges on two side surfaces, a bottom surface, and a back surface of the prepared concrete test block;

(2) providing two CCD cameras and a computer connected to the cameras, where the CCD camera includes a body and a lens, positions of the two CCD cameras are adjusted so that the CCD cameras can shoot a front surface and an upper surface that are of the concrete test block and on which no strain gauge is pasted, and a focal length of the lens of the CCD camera is adjusted to keep a distance between the lens and the concrete test block within an appropriate range to obtain a clearer and more effective image; and reducing an indoor light intensity, adding a light source, and adjusting a light intensity of the added light source so that a speckle on a surface of the concrete test block is neither too saturated nor too dark, to meet a requirement for the speckle in a DIC method, where the concrete test block is totally provided with light by the added light source to reduce impact of a light intensity caused by alternating day and night;

(3) before an experiment, first using the two CCD cameras to photograph two initial images as reference images named $f_0$ and $s_0$, and storing the images in a bmp format;

(4) if corrosion-expansion force continuously changes and a displacement and a strain on the surface of the concrete test block also continuously change as the reinforcing steel is corroded, automatically collecting, by the two CCD cameras, one image at an interval of $t_0$, starting the experiment at a moment 0, and automatically collecting two images $f_1$ and $s_1$ at a moment $t_0$;

(5) if the corrosion-expansion force continues to increase, the strain on the surface of the concrete test block continues to increase, and increasingly images are collected as the experiment proceeds, automatically collecting images $f_2$, $s_2$, $f_3$, $s_3$, $f_4$, $s_4$, . . . , $f_n$, and $s_n$ at moments $2t_0$, $3t_0$, $4t_0$, . . . , and $nt_0$, and using these collected images as target images during calculation;

(6) performing calculation by using a self-made DIC method to obtain a full-field displacement value and a full-field strain value of each image;

(7) establishing a theoretical model according to the theory of elastic mechanics and concrete deformation, to obtain a relationship between corrosion-expansion force of the reinforcing steel and a strain on a surface of the concrete test block; and (8) finally calculating a magnitude of the corrosion-expansion force of the reinforcing steel and summarizing a change rule of the corrosion-expansion force of the reinforcing steel according to the established theoretical model and the full-field displacement value and the full-field strain value obtained by using the DIC method.

A working principle of the self-made DIC method in the present invention is: two deformation field images are collected before and after deformation, correlation matching calculation is performed on speckle points on the collected images before and after the deformation, and movement of the points is tracked to obtain displacement information of a surface of an object; and specifically includes: selecting, from an image before deformation, a calculation sub-region S whose size is $(2N+1)\times(2N+1)$ and that is centered on a to-be-measured point $P(x, y)$, making the calculation sub-region S move in a target image after the deformation, and performing correlation calculation according to a normalized least square distance correlation function, to find a target sub-region S' whose size is $(2N+1)\times(2N+1)$ and that is centered on a point $P'(x+u, y+v)$ corresponding to an extreme value of a correlation coefficient C, u and v being displacements of the point $P(x, y)$ along an x direction and a y direction, respectively, and a formula for the normalized least square distance correlation function being:

$$C_{ZNSSD} = \sum_{i=-N}^{N} \sum_{j=-N}^{N} \left[ \frac{A(x_i, y_j) - A_m}{\Delta A} - \frac{B(x'_i, y'_j) - B_m}{\Delta B} \right]^2$$

$$\Delta A = \sqrt{\sum_{i=-N}^{N} \sum_{j=-N}^{N} [A(x, y) - A_m]^2}$$

$$\Delta B = \sqrt{\sum_{i=-N}^{N} \sum_{j=-N}^{N} [B(x', y') - B_m]^2}$$

$$A_m = \frac{1}{(2N+1)} \sum_{i=-N}^{N} \sum_{j=-N}^{N} [A(x, y)]^2$$

$$B_m = \frac{1}{(2N+1)} \sum_{i=-N}^{N} \sum_{j=-N}^{N} [B(x', y')]^2$$

where $A(x, y)$ is a grayscale value of the center point $P(x, y)$ of the calculation sub-region S before the deformation, and $B(x', y')$ is a grayscale value of the center point P' of the target sub-region S' after the deformation; $A_m$ and $B_m$ are averages of grayscale squares of the sub-region before the deformation and the target sub-region after the deformation; N is a positive integer, a specific value of N being set during the calculation; and $\Delta A$ is a square sum of a difference between a gray scale of each point before the deformation and an average gray scale, $\Delta B$ is a square sum of a difference between a gray scale of each point after the deformation and the corresponding average gray scale, and $C_{ZNSSD}$ represents the formula for the normalized least square distance correlation function.

A specific process of establishing the theoretical model in the present invention is: a coordinate system is established by using a center of the cross section of the reinforcing steel as a coordinate origin, wherein an x axis and a y axis are parallel to two sides of a square section of a reinforced concrete test piece, and according to the semi-inverse solution of elastic mechanics, a function of a stress component is set to $\sigma_y = f_1(y) g_1(x) q$;

the stress component is substituted into a stress formula $$\frac{\partial^2 \Phi}{\partial x^2} = f_i(y) g_i(x) q$$

and a compatible equation $$\frac{\partial^4 \Phi}{\partial x^4} + 2 \frac{\partial^4 \Phi}{\partial x^2 \partial y^2} + \frac{\partial^4 \Phi}{\partial y^4} = 0,$$

to obtain the following formula:

$$\frac{\partial^4 [f_1(y) g_3(x)]}{\partial x^4} + \frac{\partial^4 [f_1(y) g_3(x)]}{\partial x^2 \partial y^2} + \frac{\partial^4 [f_1(y) g_3(x) + x f_2(y) + f_3(y)]}{\partial y^2} = 0 \quad (1)$$

in consideration of a boundary condition, a stress condition needs to be fully satisfied on upper and lower boundaries; and in consideration of a boundary condition on a front surface, the model satisfies full contact in elastic mechanics, that is, upper and lower parts are neither disengaged from each other nor slide, and finally a stress function and a stress component are:

(2)

$$\begin{cases} \sigma_y = \frac{\partial^2 \Phi}{\partial x^2} = \left[ \left( \frac{0.2 r^2}{d(d^2 - r^2)\left(1 - \frac{1}{\sqrt{2}}\right)} y^3 + \frac{1.2 r^2}{(d^2 - r^2)} y^2 \right) \left( -2 \frac{1}{d^2} x \right) \right] q \\ \sigma_x = \frac{\partial^2 \Phi}{\partial y^2} = \left[ \left( 6 \frac{0.2 r^2}{d(d^2 - r^2)\left(1 - \frac{1}{\sqrt{2}}\right)} y + 2 \frac{1.2 r^2}{(d^2 - r^2)} \right) \right. \\ \left. \left( -\frac{1}{d^2} x^2 + 1 \right) - \left( -4 \frac{1}{d^2} \frac{0.2 r^2}{d(d^2 - r^2)\left(1 - \frac{1}{\sqrt{2}}\right)} y^3 - 4 \frac{1}{d^2} \frac{1.2 r^2}{(d^2 - r^2)} y^2 \right) \right] q \\ \tau_{xy} = -\frac{\partial^2 \Phi}{\partial y \partial x} = -\left[ \left( 3 \frac{0.2 r^2}{d(d^2 - r^2)\left(1 - \frac{1}{\sqrt{2}}\right)} y^2 + 2 \frac{1.2 r^2}{(d^2 - r^2)} y \right) \left( -2 \frac{1}{d^2} x \right) \right] q \end{cases}$$

the stress component is substituted into the following physical equation of elastic mechanics:

$$\begin{cases} \varepsilon_x = \frac{1}{E}(\sigma_x - \mu\sigma_y) \\ \varepsilon_y = \frac{1}{E}(\sigma_y - \mu\sigma_x) \\ \gamma_{xy} = \frac{2(1+\mu)}{E}\tau_{xy} \end{cases}$$

to obtain a model of the relationship between the strain on the surface of the concrete and the corrosion-expansion force of the reinforcing steel:

$$q = \frac{\varepsilon_x}{\frac{1}{E_c}\left(\frac{2.4r^2}{d^2-r^2}\right)\left(-\frac{1}{d^2}x^2+1\right)} \quad (3)$$

wherein $E_c$ is an elastic modulus of the concrete, and in order to reduce impact of different concrete test blocks on the model, the above model is modified to obtain:

$$q = \frac{k\varepsilon_x}{\frac{1}{E_c}\left(\frac{2.4r^2}{d^2-r^2}\right)\left(-\frac{1}{d^2}x^2+1\right)} \quad (4)$$

where in the equation, k is a correction coefficient, $E_c$ is the elastic modulus of the concrete; d is a side length of the surface of the concrete; r is an outer radius of the reinforcing steel, and $\varepsilon_x$, $\varepsilon_y$, and $\gamma_{xy}$ are an x-direction strain, a y-direction strain, and a shear strain of a point, respectively; $\sigma_x$, $\sigma_y$, and $\tau_{xy}$ are x-direction stress, y-direction stress, and shear stress of a point, respectively, E is an elastic modulus, $\mu$ is a Poisson's ratio, $f_1(y)$ is a to-be-determined function about y, and $g_1(x)$ is a to-be-determined function about x, so that a magnitude q of corrosion-expansion force of the reinforcing steel at any moment can be calculated according to a strain value $\varepsilon_x$ on a surface of the reinforced concrete test piece obtained by using the DIC method.

In comparison with the prior art, in the present invention, the method is simple and is characterized with safe and reliable operations, scientific principles, and low costs, so that a change in corrosion-expansion force during corrosion and expansion of reinforced concrete can be monitored in real time.

DETAILED DESCRIPTION

The present invention is further described below by using the embodiments and the accompanying drawings.

EMBODIMENT

Figure 1:
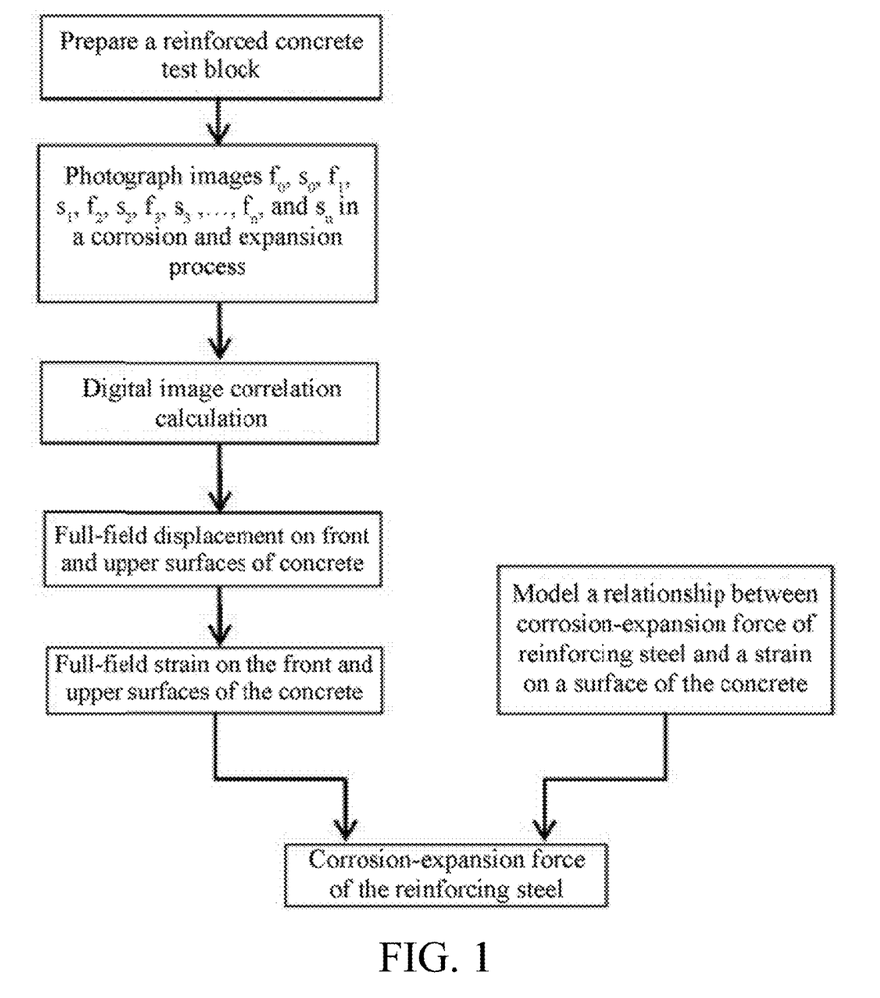
FIG. 1 is a schematic block diagram of a working principle of the present invention.
Figure 2:
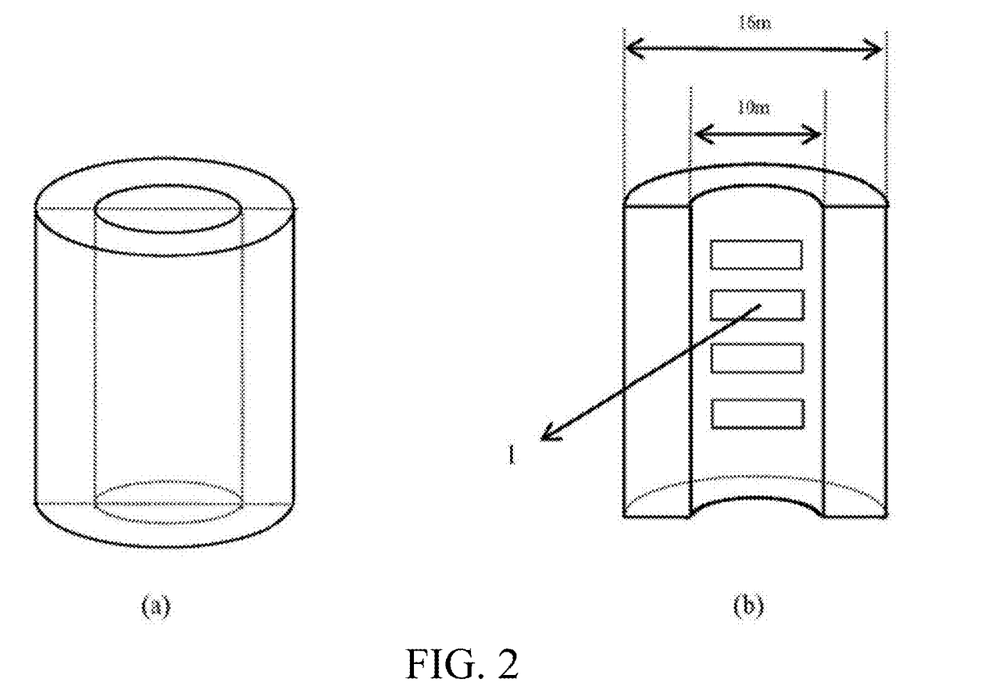
FIG. 2 shows a steel pipe (a) and a cross-sectional view (b) of the steel pipe according to an embodiment of the present invention.

In this embodiment, reinforcing steel is a hollow steel pipe, an inner diameter of the steel pipe is 10 mm, and an outer diameter is 16 mm. A strain 1 is pasted inside the steel pipe to measure strain in an inner wall of the reinforcing steel, and derive corrosion-expansion force on a surface of the reinforcing steel according to the theory of elastic mechanics, to compare the derived corrosion-expansion force with corrosion-expansion force obtained by using the method described in this example to verify validity of a measurement result. Specific steps are as follows:

(1) First, the steel pipe is longitudinally cut along an axis, and one strain gauge 1 is pasted in an inner ring of the steel pipe according to actual requirements to measure internal strain of the steel pipe.

Figure 3:
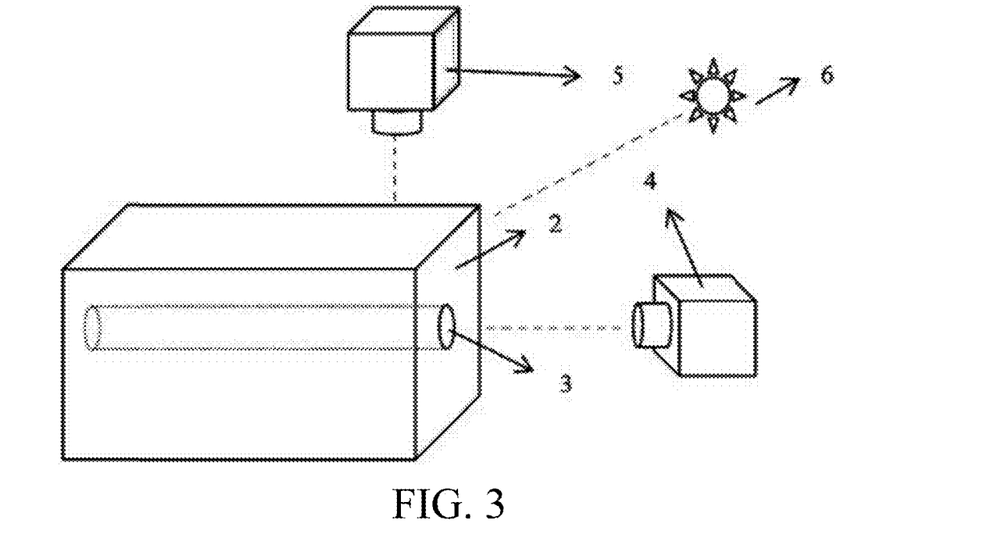
FIG. 3 is a schematic diagram of a concrete test block and a photographing system according to the present invention.

(2) A square concrete test block 2 with a steel tube 3 embedded in the middle is made, a cross section of the steel tube 3 being flush with a surface of the concrete test block. After curing for two months, strain gauges are pasted on two side surface, a bottom surface, and a rear end of the concrete test block 2, and no strain gauge is pasted on a front surface and an upper surface of the concrete test block 2, so that a CCD can collect a deformed image.

Figure 4:
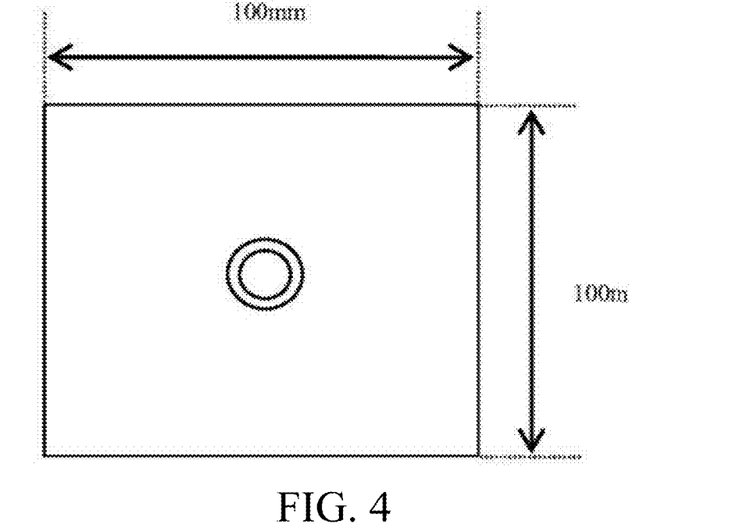
FIG. 4 is a schematic diagram of front photographing of a concrete test block according to the present invention.

(3) The concrete test block 2 is placed on an experiment bench, and a first CCD camera 4 is placed on the front of the concrete test block 2 so that the first CCD camera 4 can just photograph full-field deformation information on the front of the concrete test block 2. As shown in FIG. 4, a second CCD camera 5 is directly placed above the concrete test block 2 so that the second CCD camera 5 can just photograph the upper surface of the concrete test block 2. Due to a relatively long period of concrete cracking, it is necessary to photograph images day and night. In order to reduce impact of a light intensity caused by alternating day and night and weaken a light intensity of a laboratory, a light source 6 is added, and a light intensity of the added light source is adjusted so that a speckle on a surface of the test piece is neither too saturated nor too dark, to meet a requirement for the speckle in a DIC method.

(4) An external strain collector is connected to all strain gauges to collect strain gauge data during the experiment and store the data in real time.

(5) Before an experiment, the first CCD camera 4 and the second CCD camera 5 are used to photograph two initial images as reference images named $f_0$ and $s_0$, at the beginning of the experiment and the images are stored in a bmp format.

(6) If corrosion-expansion force continuously changes and a displacement and a strain on the surface of the concrete test block 2 also continuously change as the reinforcing steel is corroded, in order to photograph the entire cracking process of the concrete, the first CCD camera 4 and the second CCD camera 5 collect one image at an interval of $t_0=0.5$ s, the experiment starts at a moment 0, and the two CCD cameras automatically collect two images $f_1$ and $s_1$ after 0.5 s.

(7) If the corrosion-expansion force continues to increase, the strain on the surface of the concrete test block continues to increase, and increasingly more images are collected as the experiment proceeds, the CCD cameras automatically collect images named $f_2$, $S_2$, $f_3$, $S_3$, $f_4$, $S_4$, . . . , $f_n$, and $s_n$ at moments $2t_0$, $3t_0$, $4t_0$, ..., and $nt_0$, respectively, and use the collected images as target images during calculation.

(8) Calculation is performed by using a self-made DIC method to obtain a full-field displacement value and a full-field strain value of each image.

(9) A theoretical model is established according to the theory of elastic mechanics and concrete deformation, to obtain a relationship between corrosion-expansion force of the reinforcing steel and a strain on a surface of the concrete test block.

(10) A magnitude of the corrosion-expansion force of the reinforcing steel is calculated and a change rule of the corrosion-expansion force of the reinforcing steel is calculated according to the established theoretical model and the full-field displacement value and the full-field strain value obtained by using the DIC method.

Figure 5:
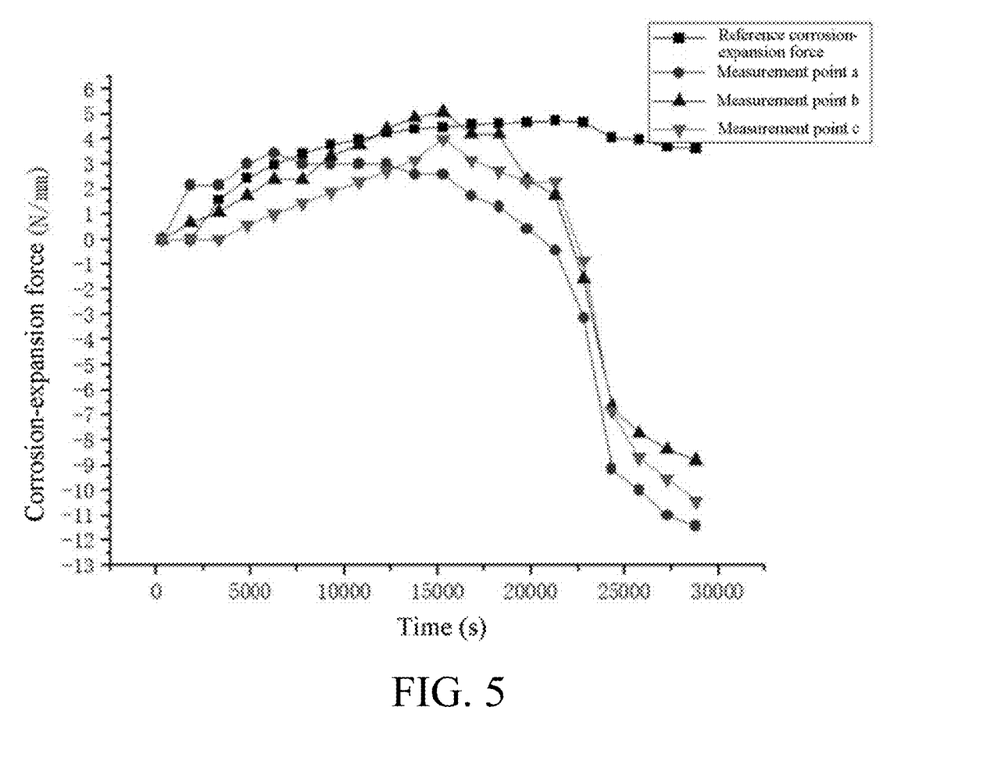
FIG. 5 is a comparison diagram of reference corrosion-expansion force and corrosion-expansion force of a measurement point according to an embodiment of the present invention.

(11) An experimental result of the obtained corrosion-expansion force is compared with corrosion-expansion force derived by a strain gauge in the inner wall of the steel pipe to verify validity of the result, and a specific experimental result is as follows:

The strain data of the surface of the concrete is substituted into formula 4, where $E_c=3\times10^4$ MPa, $k=0.6$, $\mu=0.3$, $d=500$ mm, and the result is shown in FIG. 5. The corrosion-expansion force on the surface of the steel pipe calculated by the strain gauge pasted in the inner ring of the steel pipe is used as reference corrosion-expansion force before cracking of the concrete, and corrosion-expansion force derived from strain of measurement points a, b, and c on the surface of the concrete is basically consistent with the reference corrosion-expansion force. Because the measurement points a and c are affected by a boundary of the concrete, calculated corrosion-expansion force and the corrosion-expansion force have a difference, but corrosion-expansion force calculated based on the measurement point b located in the middle of the surface of the concrete is in good agreement with the reference corrosion-expansion force. After the concrete cracks, the model fails and the Lame's solution cannot continue to be used for simplification. Therefore, the corrosion-expansion force derived from the strain on the surface of the concrete gradually begins to deviate from the reference corrosion-expansion force until the concrete is completely cracked, and the concrete is no longer subjected to hoop tensile stress. In this case, the corrosion-expansion force obtained at the measurement point completely deviates from the reference corrosion-expansion force, which is a normal phenomenon. It can be learned that the method provided in this embodiment has good applicability before the reinforced concrete structure cracks.

What is claimed is:

1. A method for measuring corrosion-expansion force during cracking of concrete due to corrosion and expansion of reinforcing steel, comprising the following steps:
    (1) first fixing reinforcing steel in the middle of a 100 mm×100 mm×300 mm mold, using stainless reinforcing steel as an electrode for electrical acceleration, and then pouring mixed concrete, so that after a cross section of the reinforcing steel is flush with a surface of the concrete, the reinforcing steel and the concrete are placed on a vibration table and vibrated for 5 minutes, and are demoulded after 24 hours and placed in a steam curing room for curing for two months to obtain a concrete test block; and pasting strain gauges on two side surfaces, a bottom surface, and a back surface of the concrete test block;
    (2) providing two CCD cameras and a computer connected to the cameras, wherein each CCD camera comprises a body and a lens, positions of the two CCD cameras are adjusted so that the CCD cameras can shoot a front surface and an upper surface of the concrete test block and on which no strain gauge is pasted, and a focal length of the lens of each CCD camera is adjusted to keep a distance between the lens and the concrete test block within a range to obtain a clear image; and reducing an indoor light intensity, adding a light source, and adjusting a light intensity of the added light source so that a speckle on a surface of the concrete test block is neither too saturated nor too dark, to meet a requirement for the speckle in a digital image correlation (DIC) method, wherein the concrete test block is totally provided with light by the added light source to reduce impact of a light intensity caused by alternating day and night;
    (3) before an experiment, first using the two CCD cameras to photograph two initial images as reference images named f0 and s0, and storing the images in a bitmap (BMP) format;
    (4) in a case that corrosion-expansion force continuously changes and a displacement and a strain on the surface of the concrete test block also continuously change as the reinforcing steel is corroded, automatically collecting, by the two CCD cameras, one image at an interval of $t_0$, starting the experiment at a moment 0, and automatically collecting two images $f_1$ and $s_1$ after said interval $t_0$;
    (5) in a case that the corrosion-expansion force continues to increase, the strain on the surface of the concrete test block continues to increase, and increasingly more images are collected as the experiment proceeds, automatically collecting images $f_2$, $s_2$, $f_3$, $s_3$, $f_4$, $s_4$, ..., $f_n$, and $s_n$, at moments $2t_0$, $3t_0$, $4t_0$, ..., and $nt_0$, and using these collected images as target images during calculation, wherein n is a positive integer;
    (6) performing calculation by using a self-made DIC method to obtain a full-field displacement value and a full-field strain value of each image;
    (7) establishing a theoretical model according to the theory of elastic mechanics and concrete deformation, to obtain a relationship between corrosion-expansion force of the reinforcing steel and a strain on a surface of the concrete test block; and
    (8) finally calculating a magnitude of the corrosion-expansion force of the reinforcing steel and summarizing a change rule of the corrosion-expansion force of the reinforcing steel according to the established theoretical model and the full-field displacement value and the full-field strain value obtained by using the DIC method.

2. The method for measuring corrosion-expansion force during cracking of concrete due to corrosion and expansion of reinforcing steel according to claim 1, wherein a working principle of the self-made DIC method is: two deformation field images are collected before and after deformation, correlation matching calculation is performed on speckle points on the collected images before and after the deformation, and movement of the points is tracked to obtain displacement information of a surface of an object; and specifically comprises: selecting, from an image before deformation, a calculation sub-region S whose size is $(2N+1)\times(2N+1)$ and that is centered on a to-be-measured point $P(x,y)$, making the calculation sub-region S move in a target image after the deformation, and performing correlation calculation according to a normalized least square distance correlation function, to find a target sub-region S' whose size is $(2N+1)\times(2N+1)$ and that is centered on a point $P'(x+u, y+v)$ corresponding to an extreme value of a correlation coefficient C, u and v being displacements of the point $P(x, y)$ along an x direction and a y direction, respectively, and a formula for the normalized least square distance correlation function being:

$$C_{ZNSSD} = \sum_{i=-N}^{N}\sum_{j=-N}^{N}\left[\frac{A(x_i, y_j) - A_m}{\Delta A} - \frac{B(x'_i, y'_j) - B_m}{\Delta B}\right]^2$$

$$\Delta A = \sqrt{\sum_{i=-N}^{N}\sum_{j=-N}^{N}[A(x, y) - A_m]^2}$$

$$\Delta B = \sqrt{\sum_{i=-N}^{N}\sum_{j=-N}^{N}[B(x', y') - B_m]^2}$$

$$A_m = \frac{1}{(2N+1)}\sum_{i=-N}^{N}\sum_{j=-N}^{N}[A(x, y)]^2$$

$$A_m = \frac{1}{(2N+1)}\sum_{i=-N}^{N}\sum_{j=-N}^{N}[B(x', y')]^2$$

wherein $A(x, y)$ is a grayscale value of the center point $P(x, y)$ of the calculation sub-region S before the deformation, and $B(x, y)$ is a grayscale value of the center point P' of the target sub-region S' after the deformation; $A_m$ and $B_m$ are averages of grayscale squares of the sub-region before the deformation and the target sub-region after the deformation; N is a positive integer, a specific value of N being set during the calculation; and $\Delta A$ is a square sum of a difference between a gray scale of each point before the deformation and an average gray scale, $\Delta B$ is a square sum of a difference between a gray scale of each point after the deformation and the corresponding average gray scale, and $C_{ZNSSD}$ represents the formula for the normalized least square distance correlation function.

3. The method for measuring corrosion-expansion force during cracking of concrete due to corrosion and expansion of reinforcing steel according to claim 1, wherein a specific process of establishing the theoretical model is: a coordinate system is established by using a center of the cross section of the reinforcing steel as a coordinate origin, wherein an x axis and a y axis are parallel to two sides of a square section of a reinforced concrete test piece, and according to the semi-inverse solution of elastic mechanics, a function of a stress component is set to $\sigma_y = f_1(y)g_1(x)q$;

the stress component is substituted into a stress formula $$\frac{\partial^2 \Phi}{\partial x^2} = f_i(y)g_i(x)q$$

and a compatible equation $$\frac{\partial^4 \Phi}{\partial x^4} + 2\frac{\partial^4 \Phi}{\partial x^2 \partial y^2} + \frac{\partial^4 \Phi}{\partial y^4} = 0,$$

to obtain the following formula:

$$\frac{\partial^2 [f_1(y)g_3(x)]}{\partial x^4} + \frac{\partial^4 [f_1(y)g_3(x)]}{\partial x^2 \partial y^2} + \frac{\partial^4 [f_1(y)g_3(x) + xf_2(y) + f_3(y)]}{\partial y^2} = 0 \quad (1)$$

in consideration of a boundary condition, a stress condition needs to be fully satisfied on upper and lower boundaries; and in consideration of a boundary condition on a front surface, the model satisfies full contact in elastic mechanics, that is, upper and lower parts are neither disengaged from each other nor slide, and finally a stress function and a stress component are:

$$\begin{cases} \sigma_y = \frac{\partial^2 \Phi}{\partial x^2} = \left[\left(\frac{0.2r^2}{d(d^2-r^2)\left(1-\frac{1}{\sqrt{2}}\right)}y^3 + \frac{1.2r^2}{(d^2-r^2)}y^2\right)\left(-2\frac{1}{d^2}x\right)\right]q \\ \sigma_x = \frac{\partial^2 \Phi}{\partial y^2} = \left[\left(6\frac{0.2r^2}{d(d^2-r^2)\left(1-\frac{1}{\sqrt{2}}\right)}y + 2\frac{1.2r^2}{(d^2-r^2)}\left(-\frac{1}{d^2}x^2+1\right)-\right.\right. \\ \left.\left(-4\frac{1}{d^2}\frac{0.2r^2}{d(d^2-r^2)\left(1-\frac{1}{\sqrt{2}}\right)}y^3 - 4\frac{1}{d^2}\frac{1.2r^2}{(d^2-r^2)}y^2\right)\right]q \\ \tau_{xy} = -\frac{\partial^2 \Phi}{\partial y \partial x} = -\left[\left(3\frac{0.2r^2}{d(d^2-r^2)\left(1-\frac{1}{\sqrt{2}}\right)}y^2 + 2\frac{1.2r^2}{(d^2-r^2)}y\right)\left(-2\frac{1}{d^2}x\right)\right]q \end{cases} \quad (2)$$

the stress component is substituted into the following physical equation of elastic mechanics:

$$\begin{cases} \varepsilon_x = \frac{1}{E}(\sigma_x - \mu\sigma_y) \\ \varepsilon_y = \frac{1}{E}(\sigma_y - \mu\sigma_x) \\ \gamma_{xy} = \frac{2(1+\mu)}{E}\tau_{xy} \end{cases}$$

to obtain a model of the relationship between the strain on the surface of the concrete and the corrosion-expansion force of the reinforcing steel:

$$q = \frac{\varepsilon_x}{\frac{1}{E_c}\left(\frac{2.4r^2}{d^2-r^2}\right)\left(-\frac{1}{d^2}x^2+1\right)} \quad (3)$$

wherein $E_c$ is an elastic modulus of the concrete, and in order to reduce impact of different concrete test blocks on the model, the above model is modified to obtain:

$$q = \frac{k\varepsilon_x}{\frac{1}{E_c}\left(\frac{2.4r^2}{d^2-r^2}\right)\left(-\frac{1}{d^2}x^2+1\right)} \quad (4)$$

wherein in the equation, k is a correction coefficient, $E_c$ is the elastic modulus of the concrete; d is a side length of the surface of the concrete; r is an outer radius of the reinforcing steel, and $\varepsilon_x$, $\varepsilon_y$, and $\gamma_{xy}$ are an x-direction strain, a y-direction strain, and a shear strain of a point, respectively; $\sigma_x$, $\sigma_y$, and $\tau_{xy}$ are x-direction stress, y-direction stress, and shear stress of a point, respectively, E is an elastic modulus, $\mu$ is a Poisson's ratio, $f_1(y)$ is a to-be-determined function about y, and $g_1(x)$ is a to-be-determined function about x, so that a magnitude q of corrosion-expansion force of the reinforcing steel at any moment can be calculated according to a strain value $\varepsilon_x$ on a surface of the reinforced concrete test piece obtained by using the DIC method.

\* \* \* \* \*